United States Patent
Kechichian et al.

(10) Patent No.: US 9,551,804 B1
(45) Date of Patent: Jan. 24, 2017

(54) MOTION DETECTION DEVICE AND CORRESPONDING METHOD

(71) Applicant: KONINKLIJKE PHILIPS N.V., Eindhoven (NL)

(72) Inventors: Patrick Kechichian, Eindhoven (NL); Warner Rudolph Theophile Ten Kate, Waalre (NL); Wilhelmus Andreas Marinus Arnoldus Maria Van Den Dungen, Boxtel (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/211,658

(22) Filed: Jul. 15, 2016

(30) Foreign Application Priority Data

Sep. 15, 2015 (EP) ..................................... 15185223

(51) Int. Cl.
*G01V 3/00* (2006.01)
*A61B 5/11* (2006.01)
(Continued)

(52) U.S. Cl.
CPC ............... *G01V 3/00* (2013.01); *A61B 5/1117* (2013.01); *G06F 1/163* (2013.01); *G08B 21/0446* (2013.01)

(58) Field of Classification Search
CPC ......... G01V 3/00; A61B 5/1117; A61B 5/681; A61B 5/1116; G08B 21/0446; G08B 21/043; G08B 21/22; G06F 1/3231; G06F 1/163; H03K 17/955; A61H 1/0262
(Continued)

(56) References Cited

U.S. PATENT DOCUMENTS 4,710,751 A * 12/1987 Webster ................. G01R 27/18
                                                         200/DIG. 2
5,682,032 A * 10/1997 Philipp .............. G06K 7/10326
                                                         235/422

(Continued)

FOREIGN PATENT DOCUMENTS

CN          204029116 U      12/2014
GB          2291204 A         1/1996
(Continued)

OTHER PUBLICATIONS

Kang et al: "Sensors on Textile Substrates for Home-Based Healthcare Monitoring"; IEEE Proceedings of the 1st Distributed Diagnosis and Home Healthcare (D2H2) Conference, Arlington, VA, Apr. 2006, pp. 5-7.

(Continued)

*Primary Examiner* — Jermele M Hollington
*Assistant Examiner* — Dustin Dickinson (57) ABSTRACT

The present disclosure relates to a wearable motion detection device (12) configured for detecting body-to-ground proximity, and to a related method. The motion detection device (12) comprising a capacitance detection unit (70) arranged to detect body-to-ground capacitance, the capacitance detection unit (70) comprising a first electrode (30) arranged to contact a body portion (16) of a monitored subject, when the device (12) is worn, a second electrode (32) that is arranged separately from but operatively connected with the first electrode (30), a shield electrode (34) that is arranged to shield the second electrode (32) from the first electrode (30), the device (12) further comprising a control unit (74) arranged to determine, under consideration of a body-to-ground capacitance signal provided by the capacitance detection unit (70), whether a fall event occurs. The present disclosure further relates to a corresponding (Continued)

computer program for implementing a motion detection method.

15 Claims, 6 Drawing Sheets

(51) Int. Cl.
 *G08B 21/04* (2006.01)
 *G06F 1/16* (2006.01)
(58) Field of Classification Search
 USPC .................................................. 340/573.1
 See application file for complete search history.

(56) References Cited

U.S. PATENT DOCUMENTS

| | | | |
|---|---|---|---|
| 2006/0077616 A1* | 4/2006 | Takiguchi | A61L 15/60 361/231 |
| 2012/0053471 A1* | 3/2012 | Aarts | A61B 5/1102 600/508 |
| 2013/0066168 A1 | 3/2013 | Yang et al. | |
| 2015/0206410 A1 | 7/2015 | Yi et al. | |
| 2015/0228177 A1 | 8/2015 | Yi et al. | |

FOREIGN PATENT DOCUMENTS

| | | |
|---|---|---|
| WO | 2014053719 A1 | 4/2014 |
| WO | 2015028283 A1 | 3/2015 |

OTHER PUBLICATIONS

Meyer et al: "Textile Pressure Sensor for Muscle Activity and Motion Detection"; IEEE, 2006, 4 Page Document.

Sergio et al: "5.4: A Textile Based Capacitive Pressure Sensor"; IEEE, 2002, pp. 1625-1630.

Sricharan et al: "Automated Human Fall Detection System Using a Fluid Dielectric, Capacitive, Multi Axial Acceleration Sensor"; 2013 3rd International Conference on Instrumentation Control and Automation (ICA), Bali, Indonesia, Aug. 2013, pp. 74-79.

* cited by examiner

MOTION DETECTION DEVICE AND CORRESPONDING METHOD

CROSS-REFERENCE TO PRIOR APPLICATIONS

This application claims the benefit of or priority of EP Application No. 15185223.3, filed on Sep. 15, 2015 which is incorporated by reference herein in its entirety.

FIELD OF THE INVENTION

The present disclosure relates to a wearable motion detection device, particularly to a fall detection device, and to a related fall detection method. More particularly, the disclosure relates to refinements in body-wearable monitoring motion detection devices and methods that incorporate proximity sensing. The present disclosure further relates to a corresponding computer program for operating a motion detection device.

BACKGROUND OF THE INVENTION

WO 2015/028283 A1 discloses a fall detection system and a fall detection method, wherein the system comprises a wearable or portable user device configured to be worn or carried by a user, the user device comprising a proximity sensor for measuring the proximity of the user device to the ground or the floor; and a movement sensor for measuring the movements of the user; the fall detection system further comprising a processing unit configured to process the measurements from the movement sensor to detect a potential fall; activate the proximity sensor if a potential fall is detected; and process the measurements from the proximity sensor to determine if the user has fallen.

In accordance with an exemplary embodiment of WO 2015/028283 A1, the proximity sensor is arranged for measuring changes in capacitance or inductance to estimate the proximity to an object. Changes in the electric or magnetic field of a capacitive or inductive proximity sensor, respectively, can indicate whether an object is in proximity to the sensor.

Fall events affect a huge number of people each year and result in significant injuries, particularly among the elderly. In fact, it has been estimated that falls are one of the top causes of death in elderly people. A fall may be defined as a sudden, uncontrolled and unintentional downward displacement of the body to the ground, followed by an impact, after which the body typically stays down on the ground. In case the fallen person is still fully conscious, he or she may push an emergency switch to ask for help. However, quite often patients are somewhat disoriented or even injured their heads and/or arms so that no deliberate alarm call may be initiated.

Therefore, automatic fall detection systems have been proposed. Conventional automatic motion detection devices are widely known and utilized in patient care environments, more particularly in the context of elderly care and geriatric care. As used herein, motion detection devices include, but are not limited to, fall detection devices. Fall detection devices may also be used in the field of child care, animal care, etc. Fall detection devices may be utilized for sleep monitoring, but also for activity monitoring.

In respect of the fall detection as such, there are several basic technical principles. Currently, fall detection systems can be divided into three main classes: body-worn, ambient-based, and a combination of the latter two.

For instance, fall detection devices are known that simply detect an impact when a monitored subject hits the ground or floor. These devices may implement conventional contact switches, for instance. Further, acceleration based devices are known that basically sense a fall event when a defined (e.g., fall acceleration or speed) kinematic threshold is met. Also combinations thereof may be envisaged.

In accordance with one type, fall detection devices are arranged as body-wearable devices. However, also stationary (remote) fall detection devices are known that may utilize optical sensing. Further, also combinations of body-wearable units and stationary units may be envisaged which may of course cause considerable manufacturing and operating efforts. Moreover, standard fall detection devices often show poor performance when discriminating real fall events from deliberate movements of the monitored subject, for instance quick movements of body limbs. Further, also relative movements between the detection device and an attachment portion (e.g. the wrist) of the monitored subject may have an adverse effect on performance, accuracy, and reliability. When the fall detection device slips out of position, a pseudo-movement may be detected, this may trigger a false alert.

Body-worn fall detection systems typically make use of on-board inertial sensors such as tri-axial accelerometers, gyroscopes, and suchlike. A combination of features derived from these signals is used to detect whether a fall has occurred at any given moment. Optionally, other sensors such as a pressure sensor can be employed to detect height changes.

Ambient-based approaches to fall detection typically employ a number of sensors placed throughout a coverage area of relevance such as the subject's premises or the clinical environment such as a hospital. These sensors include, but are not limited to video cameras and passive infrared (PIR) sensors.

Further, simple leash-based devices are known which are arranged as breakaway detection devices and may detect undesired removals from a defined location or range which triggers an alert. However, these devices are often experienced as considerably uncomfortable, error-prone and also somewhat motion restricting. Further, a breakaway-based fall detection device is basically not capable of discriminating a (horizontal) moving-away event from a (vertical) fall event.

It has been observed that sufficiently high accuracy rates may be obtained for sensors worn basically proximate to the trunk/torso and/or head of the monitored subject. The advantage of such locations is that it is symmetric (no bias due to brain function lateralization, i.e. right/left-handedness) and mainly dominated by larger and slower movements such as walking and changing postures. In particular, a combination of features based on height change and impact can exhibit better discriminative performance.

Challenges may arise when implementing such a fall detection system in a wrist-worn device. The wrists/arms of the subject are prone to faster movements and tend to undergo a larger number of pushes, impacts during daily life than the subject's torso (e.g. reaching for a twisting doorknob). Furthermore, unlike a sensor that is located on the torso or head, the posture of a person after a potential fall often cannot be reliably detected from a wrist-worn device solely employing inertial sensors due to the many degrees of freedom and position of the wrist with respect to the body.

Therefore, another approach to fall detection is to use information about the device's proximity to a surface in conjunction with inertial (acceleration) sensor signal features. After a person has fallen and an impact is detected from the accelerometer signal, or when the person (still) is falling, proximity or changes of proximity to a surface can be measured, where this surface is assumed to be the ground or floor.

There is still a need for improved or alternative motion and fall detection devices, algorithms, and related methods that further enhance the detecting reliability and that are applicable to wrist-worn monitoring systems.

SUMMARY OF THE INVENTION

In view of the above, it is an object of the present disclosure to seek for improved or alternative approaches to motion detection and fall detection and respective monitoring which may be implemented in respective methods and devices. More particularly, it is an object of the present invention to provide a motion detection device and a corresponding method that enable increased fall detection reliability and that show improved performance in discriminating real fall events from non-fall-related movements. Further, it would be advantageous to provide an enhanced motion detection system and method that enable to draw further conclusions from detected motion-related signals.

In a first aspect of the present invention a wearable motion detection device configured for detecting body-to-ground proximity is presented, the device comprising:

a capacitance detection unit arranged to detect body-to-ground capacitance, the capacitance detection unit comprising:

a first electrode arranged to contact a body portion of a monitored subject, when the device is worn,
  a second electrode that is arranged separately from but operatively connected with the first electrode,
  a shield electrode that is arranged to shield the second electrode from the first electrode,
  a control unit arranged to detect, under consideration of a body-to-ground capacitance signal provided by the capacitance detection unit, positional changes of the user.

This aspect is based on the insight that motion detection accuracy, particularly fall detection accuracy may be increased and, more generally, fall detection may be enriched by implementing the capacitance detection unit which is arranged not only to detect an impact, but also to detect an imminent or impending impact by detecting body-to-ground proximity. Hence, control unit may be arranged to determine whether a fall event occurs.

Aspects and embodiments of the disclosure will be explained and discussed herein with particular reference to fall detection related embodiments which, however, shall not be construed as limiting the scope of the disclosure. Therefore, a motion detection device in accordance with the present disclosure may be also arranged to perform additional functions, such as wearing compliance detection or even user interaction. The capacitance detection unit may be utilized in this respect since capacitance detection allows not only a (binary) switch function (i.e. contact vs. no contact state) but also a detection of intermediate states (i.e. proximity states). Therefore, the motion detection device may also be referred to as enhanced fall detection device.

For instance, the device may be capable of detecting wearing compliance, i.e. whether the user is wearing the device or not. In a particular refinement, wearing compliance may involve a determination of whether the device actually is worn properly (e.g., tightly wrapped around the wrist or arm) or not. To this end, the capacitance detection unit may provide capacitance-indicative signals which allow an assessment as to whether or not the first electrode properly contacts the skin or not.

In another example, deliberate user movements involving, but not limited to, touches, taps, knocks or even shakes may be detected and analyzed/evaluated for detecting deliberate user inputs. In this way a virtual push button may be provided, for instance. Hence, a deliberate user action/user input may be detected which may be indicative of an emergency call or a nurse call, for instance. It may be therefore beneficial to attach the device to an upper limb of the user, particularly a forearm or wrist portion.

As used herein, the first electrode may be referred to as reference electrode or reference body-contact electrode. As used herein, the second electrode may be referred to as sensor electrode or ground-approaching or ground-contacting (floor-approaching or floor-contacting) electrode. In a more general context, the first electrode may be referred to as first terminal, and the second electrode may be referred to as second terminal.

The shield electrode is basically arranged to isolate the second electrode from further (disturbing) capacitances that may be present between a first terminal formed by the first electrode and a second terminal formed by the second electrode. The undesired capacitance between the first electrode and the second electrode may be referred to as disturbing or parasitic capacitance.

Hence, the motion detection device may use the first electrode as a reference for the capacitance measurement. Between the first electrode and the second electrode a first capacitance is defined. It is noted that the first electrode is linked to the subject's body when the device is properly worn. Between the first electrode and the ground, a second capacitance is defined. Between the second electrode and the ground, a third capacitance is defined. Hence, a capacitance model circuit may be defined which includes an estimation of the expected behaviour of the capacitances when the device approaches the floor. Typically, this will induce a certain characteristic pattern or step of a capacitance signal measured by the device. Interferences between the second and the third capacitance can be reduced due to the shield electrode.

As used herein, positional changes detected by the device involve, but are not limited to, at least one of the group consisting of posture changes, fall events, tumbling events, rolling over, tossing and turning, forearm movements and further characteristic movements. Hence, in one embodiment of the device, the control unit compares a change in the capacitance measured by the capacitance detection unit to a threshold value to detect at least one of a body-to-ground contact, a body-to-ground proximity, and a body-to-ground approach.

In one exemplary embodiment, the device is arranged as an arm-wearable or wrist-wearable device comprising a belt-shaped or ring-shaped strap comprising a support layer, wherein the first electrode is arranged in an inwardly-facing fashion, wherein the second electrode is arranged in an outwardly-facing fashion, and wherein the shield electrode is arranged between the first electrode and the second electrode.

In a further exemplary embodiment, the first electrode and the second electrode are arranged such that the second electrode encompasses the first electrode. For instance, the first electrode and the second electrode may be arranged in a circumferential fashion. Preferably also the shield electrode is arranged in a circumferential fashion between the first electrode and the second electrode, wherein the first electrode, the shield electrode and the second electrode are arranged in a layered fashion, but (radially) offset from one another In an exemplary refinement of the above embodiment, the device further comprises a control case attached to the strap, wherein the control unit is arranged in the control case and wherein the control unit is operatively coupled to the first electrode, the second electrode, and the shield electrode. Hence, the device may be arranged in a wrist-watch-like fashion.

In a further exemplary embodiment, measurement electrodes of the capacitance detection unit consist of a single first electrode, a single second electrode, and a single shield electrode. In other words, the device comprises no more electrodes than the first electrode, the second electrode, and the shield electrode. Thanks the circular arrangement, there is basically no influence of the circumferential or angular orientation on the device on capacitance measurement (except for the position of the control case, if any). The electrodes form a concentric layered arrangement and preferably form a substantially full circle that comprises three layers.

In yet another exemplary embodiment, the first electrode is arranged to cling to the subject's skin at a measurement site to which the device is attached. Hence, a tight fit contact between the body of the subject (user), preferably at the wrist thereof, and the first electrode may be achieved which may provide relatively stable and steady measurement conditions.

In still another exemplary embodiment, the device further comprises a voltage follower unit for operating the shield electrode at the same potential as the second electrode. Hence, the potential difference between the second electrode, i.e. the other sensor plate, and shield electrode is effectively zero. Preferably, the shield electrode is placed in close proximity to the second electrode, which further reduces capacitance effects caused by objects below the shield electrode.

In another exemplary embodiment, the device further comprises an accelerometer unit arranged to detect body acceleration of the subject of interest, wherein the control unit is arranged to detect a fall event based on an accelerometer signal provided by the accelerometer unit and on the capacitance signal provided by the capacitance detection unit. Hence, several distinct but somewhat related signals may be utilized for detecting the fall. The accelerometer unit may detect movement as such, e.g. vertical components of the subject's movement. Further, the accelerometer may detect an impact on the floor which is typically indicated by a sudden deceleration or shock. Hence, particular fall-indicating signal patterns may be detected in the accelerometer signal which may be combined with the proximity signal.

In one exemplary embodiment, non-conductive layers are provided between the first electrode, the second electrode, and the shield electrode. Preferably, the non-conductive layers include dielectric material.

In a further exemplary embodiment, the shield electrode comprises an areal extension that is at least two times larger, preferably four times larges, than the areal extension of the second electrode, wherein the shield electrode is at least sectionally arranged as a strip comprising an axial extension that extends beyond the axial extension of the second layer. This improves the shielding performance.

In another exemplary embodiment, the device further comprises a timer module arranged to control a discharge/charge action of a capacitor one terminal of which is formed by the second electrode, wherein a discharge/charge frequency is indicative of body-to-ground proximity, when the device is worn, particularly of ground contact. Hence, a mediate proximity-indicative signal may be obtained which can be further processed and computed in the control unit. Digital data processing can be simplified. Further, the proximity-indicative signal does not necessarily have to represent a precise absolute proximity value (e.g. 10 cm, 5 cm, etc.). Rather, the proximity-indicative signal may represent a qualitative or relative proximity value.

In an exemplary refinement of the above embodiment, the timer module is further arranged to apply a defined trigger level and to apply a defined threshold level based on which the discharge/charge action is controlled. For instance, the trigger level may be utilized to initiate a charging (or recharging) cycle. Further, the threshold level may be utilized to initiate a discharge operation when a respective capacitance value is achieved. In other words, the trigger level may represent a minimum charge state and the threshold level may represent a maximum charge state between which the capacitor is operated. In some embodiments, the timer module comprises a trigger contact and a threshold contact both of which are coupled to the second electrode.

In still another exemplary embodiment, the second electrode is arranged to be coupled to a mobility aid selected from the group consisting of at least one of a walking aid, a walking frame and a wheelchair. The mobility aid may "enlarge" the second electrode and may therefore enlarge a capacitance which may be formed between the second electrode and the ground or floor.

Needless to say, a motion detection device in accordance with at least one aspect of the present disclosure may form part of a motion detection or fall detection system that implements further sensing and detecting units for implementing integrated monitoring approaches.

In a further aspect of the present invention a motion detection method utilizing body-to-ground proximity detection is presented, the method comprising the following steps:

applying a capacitance detection unit to a body portion of a subject of interest, the capacitance detection unit being arranged to detect body-to-ground capacitance and comprising:
    a first electrode arranged to contact a body portion of a monitored subject,
    wherein applying a capacitance detection unit includes arranging the first electrode to establish a contact to the body portion,
    a second electrode that is arranged separately from but operatively connected with the first electrode,
    a shield electrode that is arranged to shield the second electrode from the first electrode,
causing the capacitance detection unit to output a body-to-ground capacitance signal based on a capacitance measurement between the second electrode and the ground, and
detecting, under consideration of the body-to-ground capacitance signal, positional changes of the user Detecting positional changes of the user may involve determining whether a fall event occurs.

Preferably, a motion detection device in accordance with the present disclosure may be operated in accordance with the above method.

In yet another aspect of the present invention there is provided a computer program which comprises program code means for causing a computer to perform the steps of the method as discussed herein when said computer program is carried out on that computer.

The program code (or: logic) can be encoded in one or more non-transitory, tangible media for execution by a computing machine, such as a computer. In some exemplary embodiments, the program code may be downloaded over a network to a persistent memory unit or storage from another device or data processing system through computer readable signal media for use within the system. For instance, program code stored in a computer readable memory unit or storage medium in a server data processing system may be downloaded over a network from the server to the system. The data processing device providing program code may be a server computer, a client computer, or some other device capable of storing and transmitting program code.

As used herein, the term "computer" may stand for a large variety of processing devices. In other words, also mobile devices having a considerable computing capacity can be referred to as computing devices, even though they provide less processing power resources than standard "computers". Needless to say, such a "computer" can be part of a medical device and/or system. Furthermore, the term "computer" may also refer to a distributed computing device which may involve or make use of computing capacity provided in a cloud environment. The term "computer" may also relate to medical technology devices, fitness equipment devices, and monitoring devices in general, that are capable of processing data.

Preferred embodiments of the disclosure are defined in the dependent claims. It should be understood that the claimed method and the claimed computer program can have similar preferred embodiments as the claimed device and as defined in the dependent device claims.

BRIEF DESCRIPTION OF THE DRAWINGS

These and other aspects of the invention will be apparent from and elucidated with reference to the embodiments described hereinafter. In the following drawings

DETAILED DESCRIPTION OF THE INVENTION

In the following, main aspects and insights of the invention will be illustrated and further elucidated with reference to exemplary embodiments of fall detection methods and devices. More generally, the present disclosure relates to motion detection approaches which will be explained in more detail herein with particular reference to non-limiting fall detection embodiments. As indicated above, motion detection systems, devices and methods may be provided which are arranged in accordance with at least some embodiments of the present disclosure.

It should be noted that the following exemplary embodiments and descriptions shall be not interpreted in a limiting sense. Rather, the skilled person may readily transfer and broaden the respective specific embodiments and the components as well as process steps disclosed therein so as to arrive at the general concept of the present disclosure.

As described above in the background section, it has been found that existing fall detection methods often do not provide a sufficiently high and reliable detection rate while limiting the number of false alarms due to the movements and apparent impacts of the wrist that can occur in normal daily activities, such as walking, sitting, etc., that do not otherwise result from falls by the subject. These existing fall detection methods derive features including orientation change, height change, vertical velocity and/or impact magnitude from the movement sensor measurements to determine if the user of the fall detection system has suffered a fall.

In accordance with at least some embodiments of the present disclosure, the reliability of a wrist-worn fall detection devices may be improved by providing the device with a certain proximity sensing capability. Hence, the device may be capable of sensing the proximity of the fall detection device to the ground or floor. Proximity sensing may greatly improve the device's accuracy and detecting reliability. Proximity sensing may enhance the field of application of fall detection devices and methods.

In accordance with major embodiments of the present disclosure, proximity sensing is performed through capacitance measurement. Generally, changes in the electric magnetic field can indicate whether an object is in proximity of the sensor. A proximity-related measurement may provide a further feature basis from which fall detection approaches and algorithms may profit. For instance, a state in which a proximity signal indicates an approach and an acceleration signal indicates a quick (downward) movement clearly indicates a fall event or an impending fall.

Figure 1:
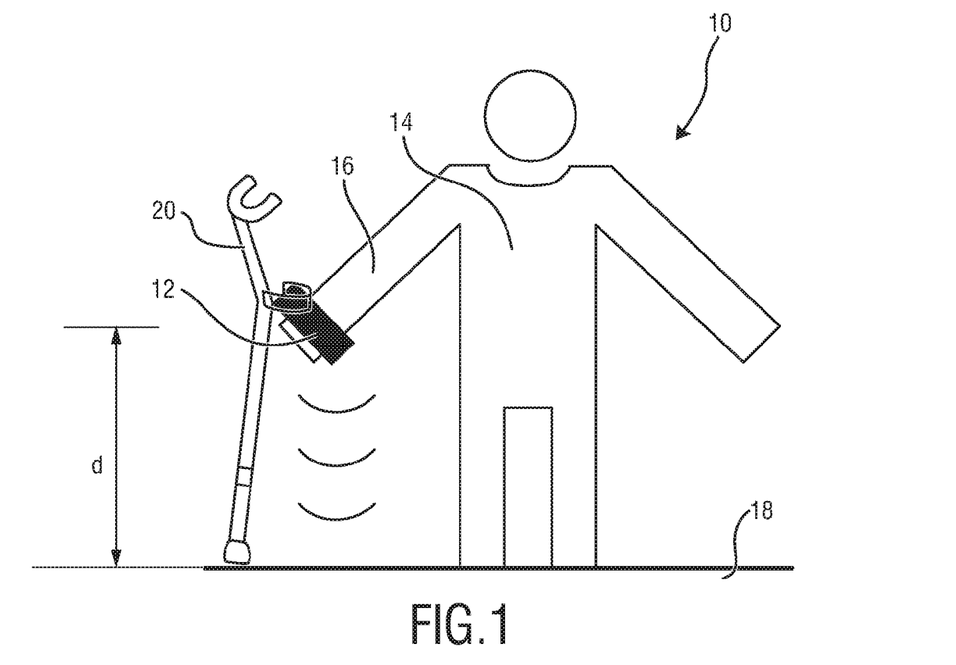
FIG. 1 shows in a simplified schematic representation of a subject wearing an exemplary embodiment of a wrist-worn motion detection system in accordance with the present disclosure, the subject being in an upright or walking orientation.
Figure 2:
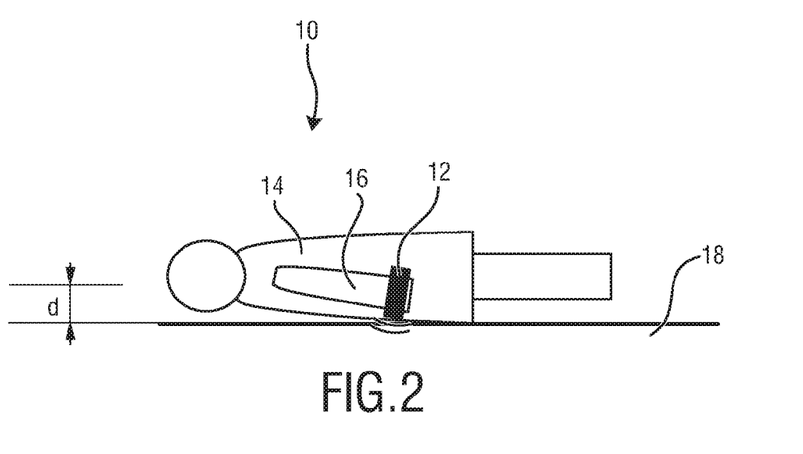
FIG. 2 shows a subject wearing a wrist-worn motion detection system in accordance with the present disclosure, with the subject lying on the ground or floor.

FIGS. 1 and 2 illustrate the use of a wrist-worn motion detection or fall detection system that utilizes a proximity sensor in determining whether a user has fallen. FIGS. 1 and 2 show schematic illustrations of a to-be-monitored subject 10, for instance an elderly person or a patient. The subject 10 is carrying or wearing a motion detection or fall detection device 12 that comprises a capacitance-based proximity sensor. It is worth mentioning that the device 12 does not necessarily have to be arranged for detecting an actual (absolute) distance (denoted by d in FIGS. 1 and 2) between the device 12 and the floor 18 in a high-precision fashion.

In the exemplary embodiment of FIGS. 1 and 2, the device 12 is attached to the subject's body 14. Particular portions of the body 14 may be used. For instance, the device 12 may be attached to a body limb 16, such as an arm or a wrist. When the subject 10 is standing or walking normally as in FIG. 1, the distance measured by the proximity sensor in the device 12 will be large, suggesting that the subject 10 is not lying on the ground or floor 18. This indicator reduces the likelihood of the fall detection algorithm detecting that a fall has taken place. Using conventional fall detection algorithms, if the subject 10 accidently bumps with its wrist against some furniture, producing a measurable impact, and there is some orientation and height change (which of course may occur in the normal movements of the subject's wrist), a fall might be detected. However, the measurement of the proximity sensor used in accordance with the present disclosure may then indicate that the wrist is not in close proximity with the floor or ground, which will reduce the likelihood of this (pseudo-fall) event being classified as a fall.

However, if the subject 10 has fallen and is lying on the ground or floor 18 as shown in FIG. 2, the distance measured by the proximity sensor in the fall detection device 12 will be small, and the detection of this feature can increase the likelihood of an actual fall being detected by the fall detection algorithm.

As illustrated in FIG. 1, the subject 10 may use a mobility aid 20, such as a cane, crutches, walkers, a wheelchair, and suchlike. The presence of the mobility aid 20 adjacent to the fall detection device 12 may have an impact on capacitance measurement. This may be regarded as a disturbing "stray capacitance". However, the presence of the mobility aid 20 and the influence on the measured capacitance associated therewith may be utilized to improve the measurement accuracy and the fall detection reliability, as will be discussed further below.

Figure 3:
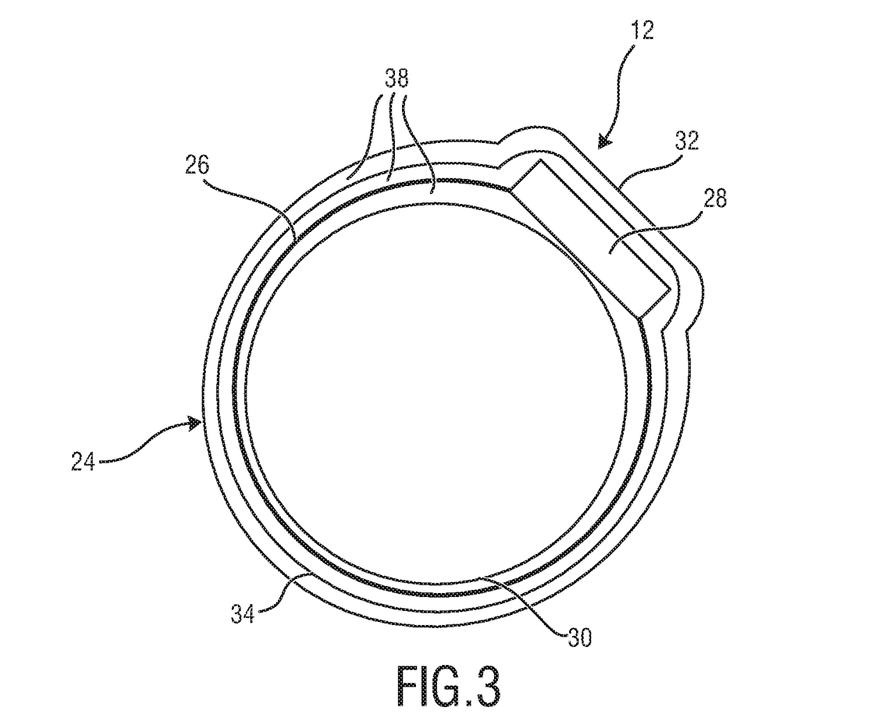
FIG. 3 shows a simplified cross-sectional view of a wearable motion detection device in accordance with an exemplary embodiment of the present disclosure.

As indicated above, capacitance-based proximity detection may contribute to reliably detecting fall events. In this context, reference is made to FIG. 3, illustrating an embodiment of a wrist-wearable motion detection or fall detection device 12. Needless to say, there may be embodiments, where the device 12 is arranged as a waist-wearable motion detection or fall detection device. Further alternative configurations may be envisaged. A plurality of devices 12 may be attached to the subject 10 at different body portions 16 thereof.

The device 12 of FIG. 3 is arranged as a ring or belt-shaped fall detecting or fall alarm device. In accordance with this embodiment, the device 12 comprises a strap (wristband) 24 which is arranged as a ring or in an annular fashion. The strap 24 comprises a support layer 26 which provides the device 12 with sufficient rigidity. A control housing or case 28 is provided which accommodates control circuitry of the device 12. Hence, the device 12 may have an integrally-shaped appearance. Alternative embodiments may be present, wherein the control circuitry is at least partially separated or remote from the strap 24.

For capacitance measurement, a first layer is provided which defines a first electrode 30. Further, a second layer is provided which defines a second electrode 32. A third layer is provided which defines a third electrode or shield electrode 34. The shield electrode 34 is arranged between the first electrode 30 and the second electrode 32. The first electrode 30 is arranged as an inner electrode. The second electrode 34 is arranged as an outer electrode. The shield electrode 34 is arranged as an intermediate electrode between the first electrode 30 and the second electrode 32. The electrodes 30, 32, 34 are ring-shaped or ring-segment-shaped and may be arranged in circular fashion as a circular stack. The strap 24 may define a loop that encompasses and delimits an interior space 36 in which a body portion 16 (e.g. the wrist) of the subject 10 is placed when the device 12 is in use.

Preferably, the first electrode 30 is, in the attached state of the device 12, arranged adjacent to or in close proximity with the surface of the body portion 16. Hence, the first electrode 30 may also be referred to as reference electrode or body electrode herein, and vice versa. Preferably, the first electrode 30 is at least slightly biased against the body portion 16. The first electrode 30 so-to-say shortcuts or connects the body and a reference terminal at the device 12.

The second electrode 32 is offset or spaced away from the first electrode 30 and may be therefore referred to as sensor electrode, and vice versa. Preferably, the first electrode 30 and the second electrode 32 are not directly coupled to one another in conductive fashion. Hence, a capacitance may be defined between the first electrode 30 and the second electrode 32. However, it is desirable that the capacitance between the first electrode 30 and the second electrode 32 becomes not too large. To this end, the third electrode 34 is provided which is arranged as an electromagnetic barrier between the first electrode 30 and the second electrode 32. The third electrode 34 shields the second electrode 32 from the first electrode 30.

Generally, the electrodes 30, 32, 34 may be formed from conductive material. However, preferably there is no direct conductive interconnection between any of the electrodes 30, 32, 34. Hence, between each pair of the electrodes 30, 32, 34 a respective capacitance may be defined wherein the electrodes 30, 32, 34 form respective opposite terminals thereof.

Between the first electrode 32 and the shield electrode 34, and between the shield electrode 34 and the second electrode 32, respectively, non-conductive layers 38 may be present, e.g. a non-conductive potting or sealing. Any non-conductive layer further stiffens the strap 24. The electrodes 30, 32, 34 may be at least partially embedded in the non-conductive material. The electrodes may be (axially) aligned and arranged in a layered fashion (radially) offset from one another. In terms of axial extension or width extension, the shield electrode 34 is preferably larger than at least one of the first electrode 30 and the second electrode 32. Hence, the shield electrode 34 may cover and axially overlap at least one of the first electrode 30 and the second electrode 32 which improves shielding.

Needless to say, there may be alternative non-circular embodiments of the strap 24 and the electrodes 30, 32, 34 extending in two dimensions. Hence, the strap 24 may be arranged as a basically flat layered pad or band.

A potential issue for capacitance-based proximity sensing utilizing mobile devices is that the object or surface which forms the reference for the proximity measurement, is usually assumed to be at the same reference potential as that of the measurement device. For a wrist-based device, this basically cannot always be the case since there is no direct connection between the measurement device's reference and that of the object which is the floor or ground 18 (also referred to as earth herein).

Generally, capacitive proximity sensing is based on measuring a sensor's capacitance changes as a representative of its changing proximity to an object or surface. This change in proximity typically depends on the object's size, distance, material and composition. Typically, a capacitor is formed by two conductive plates or terminals with either air or another type of dielectric material present between them. The capacitance, in Farads (F) between two conductive plates is given by $$C = \epsilon_r \epsilon_0 \frac{A}{d} \quad (1)$$

wherein A denotes the area between the overlapping conductive plates or electrodes, and d is the distance between them. The electric permittivity of vacuum and dielectric constant of the material between the two plates are denoted by $\epsilon_0$ and $\epsilon_r$, respectively. It will be appreciated by those skilled in the prior art that other geometries, including sphere-plane and cylinder-plane exist. The above shall be construed as an illustrative description of proximity-sensing fundamentals, and shall not be construed as limiting the scope.

Figure 4:
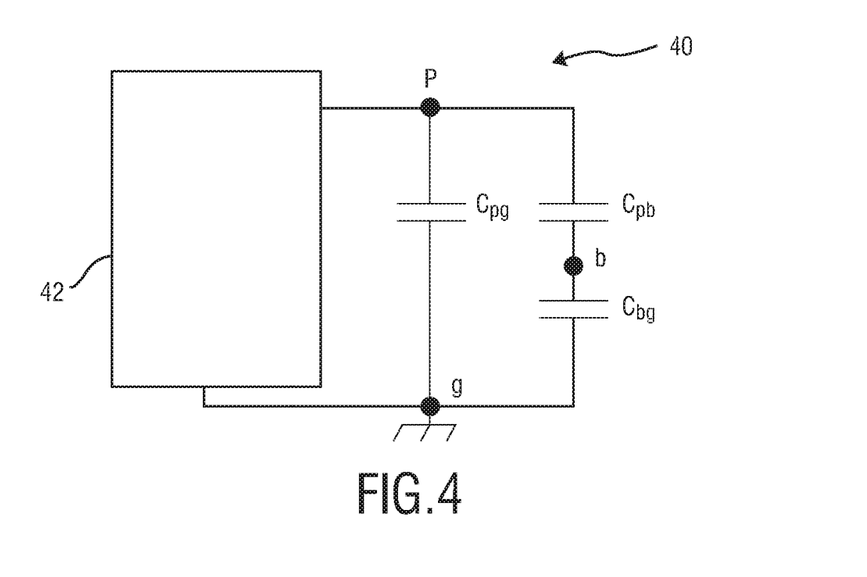
FIG. 4 illustrates an explanatory model circuit for capacitive proximity sensing.

FIG. 4 illustrates a rather simplified schematic model representation of an exemplary capacitance-based proximity detection system 40, for example, a capacitive push button or switch. The system 40 comprises a measurement circuit 42 and contacts, electrodes or nodes between which capacitances may be defined. For instance, node g represents ground or earth. Further, node p represents a sensor plate or electrode. Node b represents a body portion or limb, such as a finger of a user. Between the nodes p and g, a capacitance $C_{pg}$ may be present. Between the nodes p and b, a capacitance $C_{pb}$ may be present. Between the nodes b and e, a capacitance $C_{be}$ may be present. As a subject's finger (or limb) approaches the button of the proximity detection system 40, the capacitance $C_{pb}$ between the node p and the finger b increases and accordingly a "push" may be detected.

The measurement circuit 42 measures the capacitance $C_{pg}$ between its measuring node (push button sensor electrode) p and ground g. If the capacitance between the subject's body and ground, $C_{bg}$, is assumed to be much higher than the capacitance between the push button sensorp and the subject's finger (which is essentially part of his or her body), $C_{pb}$, then this latter capacitance can be reliably measured and the proximity detected. The capacitance $C_{pg}$ between the push button sensor node p and ground g, can be reduced via the introduction of a shield electrode which is driven at the same potential as the electrode p and placed in close proximity to electrode p to shield it from earth or ground node g.

Figure 5:
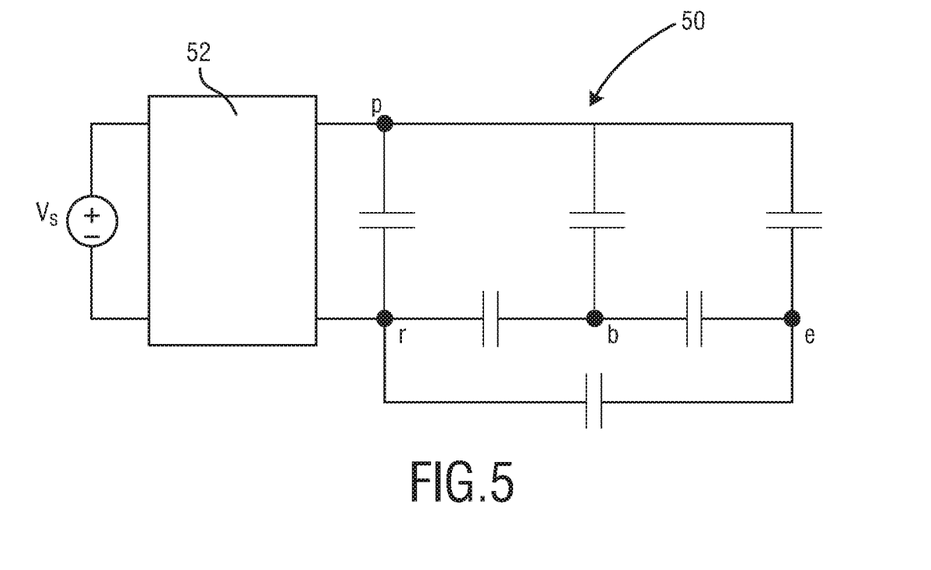
FIG. 5 illustrates an extended explanatory model circuit for capacitive proximity sensing.

Further reference is made to FIG. 5 illustrating a proximity detection system 50 implementing a measurement circuit 52 (including a voltage supply $V_s$). The proximity detection system 50 is arranged as part of a mobile (e.g. wrist-worn or wrist-wearable) device. In contrast to the illustration of FIG. 4, the model of the proximity detection system 50 of FIG. 5 further comprises a reference electrode or node r. In this embodiment, the device's reference node r is not at the same potential as the earth node e which may introduce a large number of additional capacitances that affect the measurement of $C_{be}$. Between the nodes p, r, b and e, capacitances $C_{re}$, $C_{pe}$, $C_{be}$, $C_{rb}$, $C_{pb}$ and $C_{rp}$ may be present. The measured capacitance $C_m$ corresponds to the capacitance $C_{rp}$ between nodes p and r.

Assuming that proper shielding of the sensor plate node p may be applied, the capacitances between nodes p and r, and nodes p and b can be reduced, resulting in a measured capacitance that is given by $$C_m = \frac{\left(C_{re} + \frac{C_{rb}C_{be}}{C_{rb} + C_{bs}}\right)}{1 + \frac{C_{re}}{C_{pe}} + \frac{C_{rb}C_{be}}{(C_{rb} + C_{be})C_{pe}}} \quad (2)$$

Even if the sensor plate node p is in direct contact with the earth or ground node e, i.e. $C_{pe} \rightarrow \infty$, the measured capacitance $C_m$ still contains the effects of the capacitances $C_{re}$ and $C_{rb}$ which reduces the accuracy of the measurement.

A beneficial approach may be therefore to place the device's reference electrode/node r in direct contact with the subject's wrist/body b such that the resulting equivalent electric model basically can be reduced to that of FIG. 4 (in terms of the number of nodes and capacitances therebetween).

Figure 6:
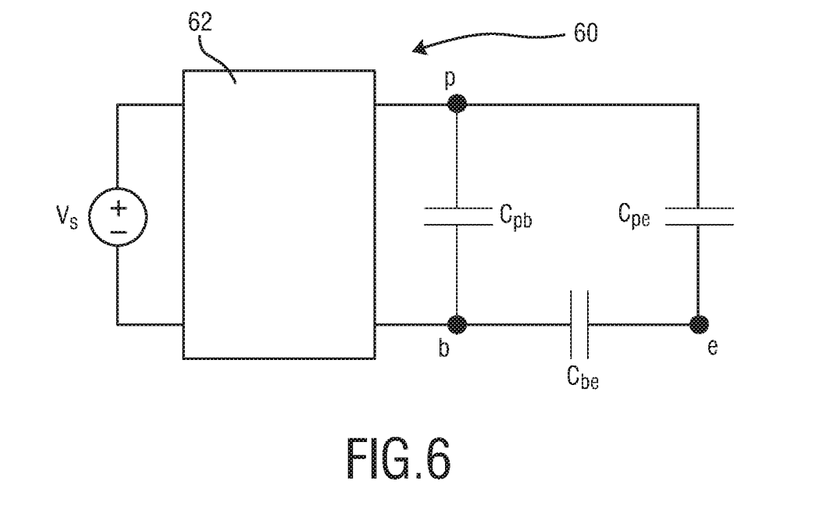
FIG. 6 illustrates a simplified explanatory model circuit for capacitive proximity sensing in accordance with the present disclosure.

FIG. 6 illustrates the resulting simplified model obtained by connecting or coupling nodes b and r directly to one another. The proximity detection system 60 comprises a measurement circuit 62 having a reference terminal or node b which is arranged to be coupled to the body of the monitored subject, and a sensor (plate) node p. An earth or ground node is denoted by e. Between nodes p and b, a capacitance $C_{pb}$ may be present which corresponds to the measured capacitance $C_m$. Between nodes p and e, a capacitance $C_{pe}$ may be present. Between nodes b and e, a capacitance $C_{be}$ may be present.

In accordance with at least some embodiments of the present disclosure, the capacitance $C_{pb}$ between the sensor plate p and the wrist b may be reduced with proper shielding, resulting in a measured capacitance equal to $$C_m = \frac{C_{be}C_{pe}}{C_{be} + C_{pe}} \quad (3)$$

For $C_{be} \gg C_{pe}$, the above measured capacitance in (3) is $C_m < C_{pe}$. As the sensor plate approaches the earth, i.e. during a fall, the value of $C_m$ rises and approaches the value of $C_{be}$. In the limit where the sensor plate p is in close contact with the ground e and $C_{pe} \rightarrow \infty$, $C_m = C_{be}$. Therefore, by coupling the device reference r to the subject's body b, the measured capacitance $C_m$ is a more accurate representation of the capacitance $C_{be}$ between the body and earth, especially after a fall has taken place.

Figure 7:
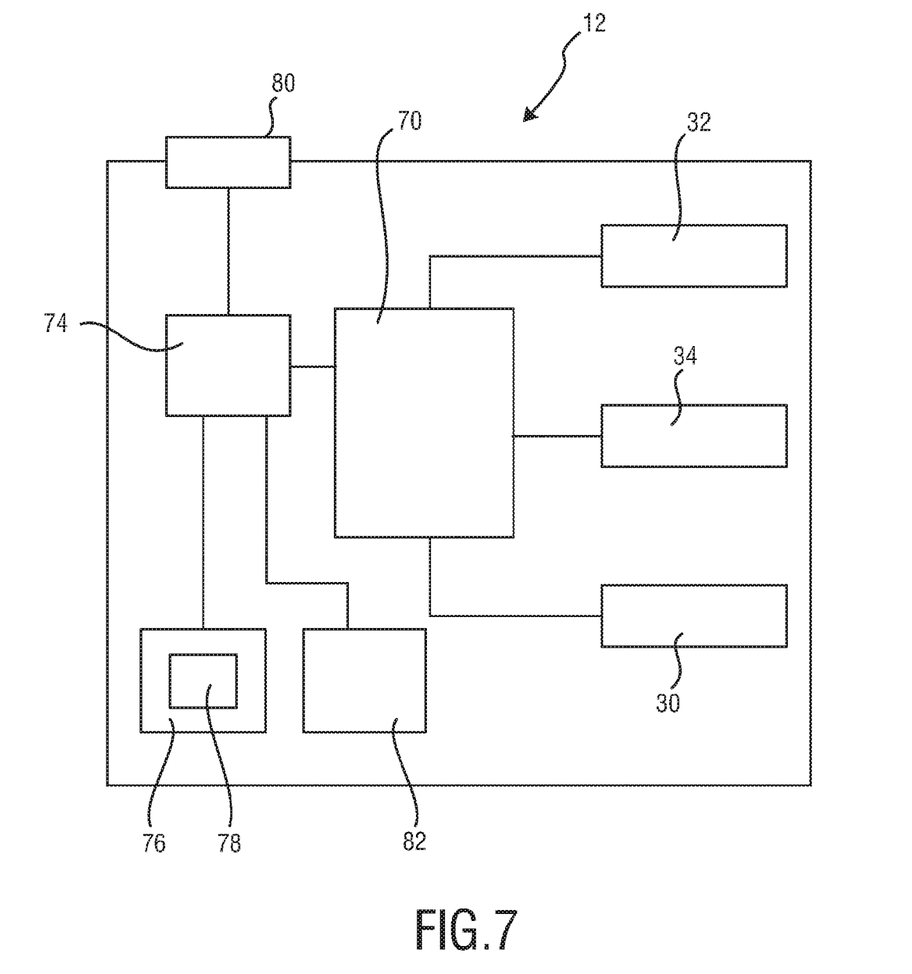
FIG. 7 shows a schematic block diagram of an exemplary embodiment of a proximity-sensing motion detection device in accordance with the present disclosure.

A simplified block representation of a motion detection device 12 in accordance with the present disclosure is shown in FIG. 7. The system 12 is provided with a first electrode 30 (also referred to as reference or body electrode herein), a second electrode 32 (also referred to as sensor-plate electrode herein), and a shield electrode 34. The electrodes 30, 32, 34 are coupled to a measurement circuit which is refereed to herein as capacitance detection unit 70. The motion detection device 12 further comprises a control unit 74 which is operable to process signals delivered thereto from the capacitance detection unit 70, and from further components of the fall detection device 12. Needless to say, a battery or a similar energy storage unit may be provided for powering the fall detection device 12.

In some embodiments, the fall detection device 12 further comprises a (supplemental) accelerometer unit 76 that comprises at least one acceleration/intertial sensor 78. Hence, supplemental motion-indicating signals may be delivered to the control unit 76.

Further, the motion detection device 12 may comprise at least one interface 80, particularly a data exchange interface. The interface 80 may be a wireless interface or a non-wireless (tethered) interface, for instance. Further, a battery charging interface may be provided. In some embodiments, an alert outputting unit 82 may be provided which for instance outputs an alert sound when the subject wearing the device 12 has been falling or tumbling to the ground. Further, the device 12 may be arranged for outputting a silent alert (remote transmission alarm) signal via the interface 80 to inform nurses, caregiver or relatives about a fall or tumble event.

Figure 8:
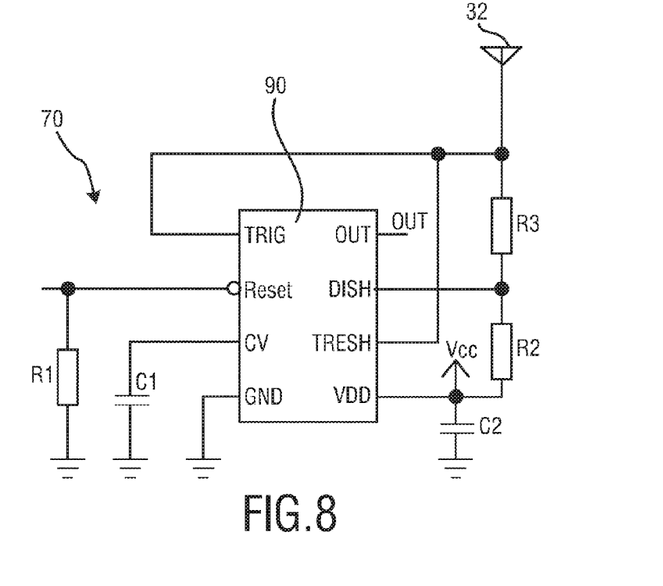
FIG. 8 shows an exemplary embodiment of control circuitry for use in a proximity-sensing motion detection device in accordance with the present disclosure.

FIG. 8 illustrates an exemplary embodiment of a capacitance detection unit 70 in accordance with the present disclosure which is arranged for proximity sensing. In accordance with this embodiment, the capacitance detection unit 70 comprises a timer module 90. By way of example, the timer module 90 comprises a timer microcontroller such as the TLC555 (available from Texas Instruments) and similar microcontrollers.

In accordance with the arrangement of FIG. 8, the timer module 90 is implemented as an astable multi-vibrator. A sensor electrode (second electrode) 32 is coupled to or provided in the timer module 90. The timer module 90 has a trigger and threshold level, such that when the trigger input is above the trigger level and the threshold input is above the threshold level the output is set to low, and the capacitor is allowed to discharge. Once the trigger value falls below the trigger level, the output goes high and the capacitor begins to recharge.

It is noted that with the embodiment of FIG. 8, the capacitive sensor electrode 32 is connected to both TRIG (trigger) and THRESH (threshold) inputs. That is why the circuit is named an astable multi-vibrator circuit. The trigger and threshold levels correspond to approximately one-third, and two-thirds of the supply voltage Vcc, respectively. The discharge terminal provides a low-impedance path to the module's reference (ground) whenever the output is low. Thus during periods when the output is high, the capacitor is allowed to charge via the resistors R2 and R3, and when it is low, it discharges to ground through resistor R3. The resulting signal is composed of pulses with widths directly proportional to the virtual capacitance between the sensor and nearby objects/surfaces.

As a result of the exemplary implementation in accordance with FIG. 8, when the virtual capacitance between the transmitter electrode and an object is large, it takes longer for the electrode to charge, and therefore its charge/discharge frequency is low. When this capacitance is low, the charge/discharge frequency increases. Therefore, for a given period, the capacitance of the sensor is inversely proportional to the number of charge/discharge cycles. This approach for measuring the relative capacitance is used in at least some embodiments of the present disclosure. The capacitance and charge/discharge frequency are related via $$C = \frac{1}{f_{sens}(R2 + 2R3)\ln 2} \quad (4)$$

wherein $f_{sens}$ is the measured charge/discharge frequency, and R2/R3 correspond to the resistances in FIG. 8. It is worth noting in this context that the capacitance C measured by the above circuit is with respect to the circuit's own reference or ground potential.

Those skilled in the prior art will appreciate and readily understand that there are other ways to measure capacitance such as an LC resonator circuit, where changes in the measured resonance frequency correspond to a changes in the capacitance C. Hence, the above exemplary embodiment shall not be construed in a way limiting the scope of the present disclosure.

Figure 9:
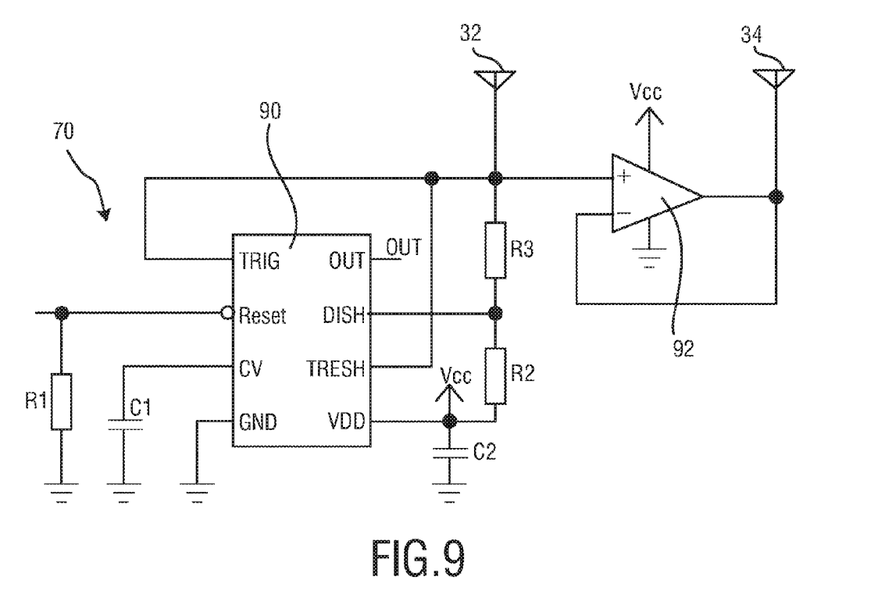
FIG. 9 shows an extended exemplary embodiment of control circuitry for use in a proximity-sensing motion detection device in accordance with the present disclosure.

With reference to FIG. 9, a further exemplary embodiment of a capacitance detection unit 70 in accordance with at least some aspects of the present disclosure is described. As with the embodiment of FIG. 8, a timer module 90 may be provided. Further, a shield electrode 34 is provided which is coupled to the timer module 90 via a voltage follower 92 and arranged to shield the sensor electrode (second electrode) 32.

In general, and unlike other proximity sensors such as infrared and ultrasound, capacitive sensing is omnidirectional. This may pose challenges for wearable devices where the unwanted effects of the subject's wrist or limb on the measured capacitance should be minimized as much as possible. To this end, the shield electrode 34 may be employed which is driven at the same potential as the sensor plate electrode 32 via a voltage follower circuit 92. When the shield electrode 34 is placed in close proximity to the sensor plate electrode 32, any capacitance effects caused by objects below the shield electrode 34 are minimized to a certain extent since the potential difference between the sensor plate electrode 32 and shield electrode 34 is effectively zero.

Further reference is made to FIG. 9 and to FIG. 3. In accordance with at least some embodiments disclosed herein, size and placement of the electrodes 30, 32, and 34 are important for improving the overall performance of the measured capacitance $C_m$ as described in equation (3). In the following, recommendations for the placement of these electrodes 30, 32, and 34 are provided in the context of a wrist-wearable device implementation. The relative size of the shield electrode 34 with respect to the sensor plate electrode 32 also influences the measured capacitance $C_m$. It has been found that a shield with an area of at least 2 times larger, preferably about 4 time larger, than the area of the sensor plate electrode 32 is sufficient to block the effects of unwanted objects or the body of the capacitance measurement to a certain extent.

It will be therefore appreciated and readily understood by those skilled in the art that other configurations are possible depending on the specific application (e.g. belt device). Hence, the above shall not be construed in a limiting sense, but rather as an illustrative elucidation of one of numerous exemplary embodiments that fall within the scope of the present disclosure.

It will also be appreciated and readily understood by those skilled in the prior art that another exemplary embodiment of the system proposed in FIGS. 6 and 7 may be to place the sensor plate electrode 32 in contact with the body instead of the reference. Various sensor configurations with respect to the system of FIG. 6 may be envisaged.

Having explained the configuration and the way of operation in more detail, again reference is made to FIG. 3 which may implement a capacitance detection unit 70 as illustrated in FIG. 9 in the device 12. As shown there, an inner face of the strap or wrist band 24 may be composed of the reference electrode 30 which maintains contact with the subject's wrist as long as the device is worn properly. In this same embodiment, in an outer region of the wrist band 24 the shield electrode 34 is provided which may also encompass the control case 28 in which main control components of the device 12 may be accommodated. Finally a very thin non-conductive material 38 followed by the sensor-plate electrode 32 is placed on top of this material is provided. It is noted that this embodiment is presented as comprising plates arranged on the outside and inner face of a wrist device. However, these electrodes may also be placed in the same order within the wrist-device and band.

It can be appreciated that while the electrode placement shown in FIG. 3 successfully shields the sensor plate electrode 32 from the effects of the wrist, the sensor-plate electrode 32 can still capture the effects of the subject's body, e.g. torso, legs, head, when approaching these parts. This leads to a non-negligible capacitance $C_{pb}$ which can considerably increase the measured capacitance $C_m$. In some embodiments such an effect may be desirable, for example if activities such as walking should be detected. In the case of falling, such a sensor configuration also leads to a drop in measured capacitance as the arms move away from the body in a bracing motion followed by a sharp increase after impact.

In another exemplary embodiment, the sensor-plate electrode 32 may be limited to the area of the device 12 around the control case 28 such that the effects of the subject's own body 14 are limited. This may somewhat reduce the fall detection accuracy, especially if the wrist falls flat on the ground. Nevertheless in some applications, this may be a viable beneficial option.

In another exemplary embodiment, the wrist-worn device 12 comprises of a wider or longer sensor-plate electrode 32 which can be wind up (or wrapped around) the lower arm. This may increase the sensor-plate surface area and therefore improve the body-to-ground capacitance measure for the detection of falls. Hence, at least one of the electrodes 30, 32, 34 may be arranged in a belt-like or strap-like fashion (e.g. not as a closed ring).

In another exemplary embodiment, in particular for increased sensitivity to detect different postures and activity, a dangling or hanging wire from the device sensor-plate electrode 32 maintains direct contact with the earth. This may result in $C_{pe} \rightarrow \infty$ and $C_m = C_{be}$. In a similar embodiment, the sensor-plate electrode 32 may be coupled to a walking aid 20 (FIG. 1) device such as a walking cane/stick or crutches. This considerably increases the capacitance $C_{pe}$ leading to a very accurate estimate of $C_{be}$ for fall detection.

Also these embodiments may profit from the shield electrode 34 which isolates the first and the second electrodes 30, 32 from one another.

Figure 10:
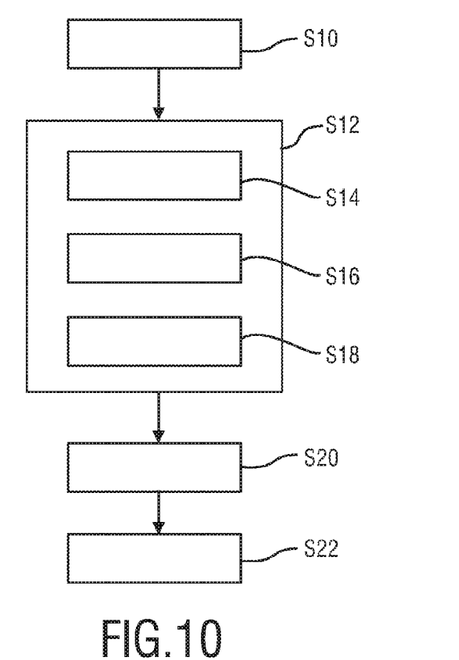
FIG. 10 shows an illustrative block diagram representing several steps of an exemplary embodiment of a proximity-sensing motion detection method in accordance with the present disclosure.

Reference is made to FIG. 10, illustrating a simplified block diagram exemplifying an embodiment of a fall detection method utilizing body-to-ground proximity detection method in accordance with the present disclosure. Initially, in a step S10 a capacitance detection unit is provided which may form part of a mobile, particularly a wrist-wearable fall detecting device.

In a further step S12 a layered arrangement of electrodes is provided and arranged in a defined fashion with respect to a body portion (particularly a body limb, such as a wrist portion) of a monitored subject. Step S12 involves (sub) steps S14, S16, S18. In a (sub)step S14, a first electrode is arranged in close contact with the body portion. In a (sub)step S16, a second electrode is arranged such that the second electrode is offset from the first electrode. The second electrode may be outwardly spaced away from the first electrode. In a (sub)step S18, a shield electrode may be arranged between the first electrode and the second electrode to shield them from one another. The electrodes may form a layered ring of band-like or strap-like electrodes.

In a further step S20 a measurement circuit is operated so as to obtain a body-to-ground proximity representative capacitance signal. In a subsequent step S22 it is determined whether a fall event occurs, under consideration of the body-to-ground capacitance signal.

Figure 11:
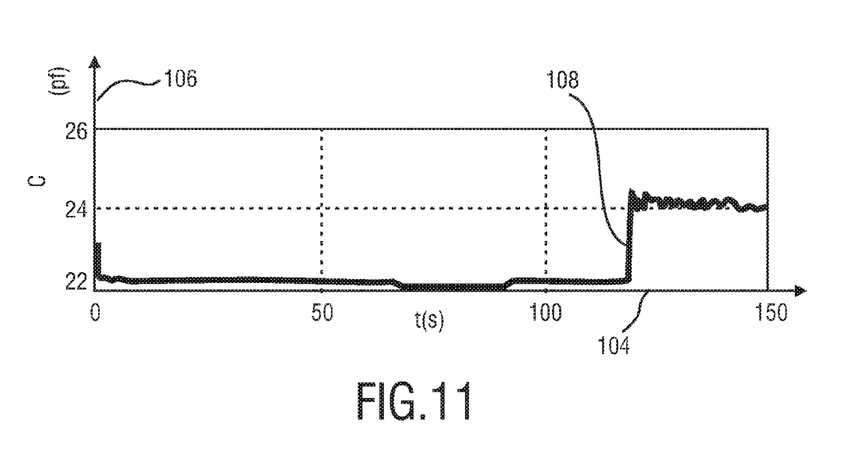
FIG. 11 shows a chart illustrating an exemplary capacitance over time curve of a proximity-sensing motion detection device indicating a fall event.

FIG. 11 illustrates an exemplary temporal chart 108 of a measured capacitance $C_m$ detected by a device in accordance with a present disclosure. In axis of abscissa 104 denotes time t (in seconds). An ordinate axis 106 denotes capacitance (in picofarad, pF). A fall of the subject to the ground occurs at about a time t=120 sec, leading to an increase of about 2 pF in the measured capacitance chart 108. The fall is represented by a distinct step in the signal chart 108.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A wearable motion detection device configured for detecting body-to-ground proximity, the device comprising:
    a capacitance detection unit arranged to detect body-to-ground capacitance, the capacitance detection unit comprising:
        a first electrode arranged to contact a body portion of a monitored user, when the device is worn,
        a second electrode that is arranged separately from but operatively connected with the first electrode,
        a shield electrode that is arranged to shield the second electrode from the first electrode,
    a control unit arranged to detect, under consideration of a body-to-ground capacitance signal provided by the capacitance detection unit, positional changes of the user.

2. The device as claimed in claim 1, wherein the control unit compares a change in the capacitance measured by the capacitance detection unit to a threshold value to detect at least one of a body-to-ground contact, a body-to-ground proximity, and a body-to-ground approach.

3. The device as claimed in claim 1, wherein the device is arranged as an arm-wearable or wrist-wearable device comprising a belt-shaped or ring-shaped strap comprising a support layer, wherein the first electrode is arranged in an inwardly-facing fashion, wherein the second electrode is arranged in an outwardly-facing fashion, and wherein the shield electrode is arranged between the first electrode and the second electrode.

4. The device as claimed in claim 3, wherein the first electrode and the second electrode, preferably also the shield electrode, are arranged, such that the second electrode encompasses the first electrode.

5. The device as claimed in claim 4, further comprising a control case attached to the strap, wherein the control unit is arranged in the control case and wherein the control unit is operatively coupled to the first electrode, the second electrode, and the shield electrode.

6. The device as claimed in claim 1, wherein measurement electrodes of the capacitance detection unit consist of a single first electrode, a single second electrode, and a single shield electrode.

7. The device as claimed in claim 1, wherein the first electrode is arranged to cling to the subject's skin at a measurement site to which the device is attached, and wherein preferably non-conductive layers are provided between the first electrode, the second electrode, and the shield electrode.

8. The device as claimed in claim 1, further comprising a voltage follower unit for operating the shield electrode at the same potential as the second electrode.

9. The device as claimed in claim 1, further comprising an accelerometer unit arranged to detect body acceleration of the subject of interest, wherein the control unit is arranged to detect a fall event based on an accelerometer signal provided by the accelerometer unit and on the capacitance signal provided by the capacitance detection unit.

10. The device as claimed in claim 1, wherein the shield electrode comprises an areal extension that is at least two times larger, preferably four times larger, than the areal extension of the second electrode, wherein the shield electrode is at least sectionally arranged as a strip comprising an axial extension that extends beyond the axial extension of the second layer.

11. The device as claimed in claim 1, further comprising a timer module arranged to control a discharge/charge action of a capacitor one terminal of which is formed by the second electrode, wherein a discharge/charge frequency is indicative of body-to-ground proximity, when the device is worn, particularly of ground contact.

12. The device as claimed in claim 11, wherein the timer module is further arranged to apply a defined trigger level and to apply a defined threshold level based on which the discharge/charge action is controlled.

13. The device as claimed in claim 1, wherein the second electrode is arranged to be coupled to a mobility aid selected from the group consisting of at least one of a walking aid, a walking frame and a wheelchair.

14. A motion detection method utilizing body-to-ground proximity detection, the method comprising the following steps:
  applying a capacitance detection unit to a body portion of a subject of interest, the capacitance detection unit being arranged to detect body-to-ground capacitance and comprising:
    a first electrode arranged to contact a body portion of a monitored user,
    wherein applying a capacitance detection unit includes arranging the first electrode to establish a contact to the body portion,
    a second electrode that is arranged separately from but operatively connected with the first electrode,
    a shield electrode that is arranged to shield the second electrode from the first electrode,
  causing the capacitance detection unit to output a body-to-ground proximity capacitance signal based on a capacitance measurement between the second electrode and the ground, and
  detecting, under consideration of the body-to-ground capacitance signal, positional changes of the user.

15. Computer program comprising program code means for causing a computer to carry out the steps of the method as claimed in claim 14 when said computer program is carried out on a computer.

* * * * *